(12) United States Patent
Andersson

(10) Patent No.: US 10,848,882 B2
(45) Date of Patent: Nov. 24, 2020

(54) IMPLANT ABUTMENT

(71) Applicant: Marcus Andersson, Gothenburg (SE)

(72) Inventor: Marcus Andersson, Gothenburg (SE)

(73) Assignee: Cochlear Limited, Macquarie University (AU)

( * ) Notice: Subject to any disclaimer, the term of this patent is extended or adjusted under 35 U.S.C. 154(b) by 247 days.

(21) Appl. No.: 15/888,628

(22) Filed: Feb. 5, 2018

(65) Prior Publication Data

US 2018/0234780 A1    Aug. 16, 2018

Related U.S. Application Data

(63) Continuation of application No. 14/685,048, filed on Apr. 13, 2015, now Pat. No. 9,888,329, which is a continuation of application No. 12/601,801, filed as application No. PCT/SE2008/000337 on May 20, 2008, now Pat. No. 9,005,202.

(30) Foreign Application Priority Data

May 24, 2007 (SE) ........................................ 0701244

(51) Int. Cl.
*H04R 25/00* (2006.01)
*A61F 2/00* (2006.01)

(52) U.S. Cl.
CPC ......... *H04R 25/606* (2013.01); *A61F 2/0077* (2013.01); *H04R 2225/67* (2013.01); *H04R 2460/13* (2013.01)

(58) Field of Classification Search
CPC .............................. A61F 2/0077; H04R 25/606
See application file for complete search history.

(56) References Cited

U.S. PATENT DOCUMENTS

| | | |
|---|---|---|
| 3,043,000 A | 7/1962 | Hatfield |
| 3,487,403 A | 12/1969 | Pihl |
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |

(Continued)

FOREIGN PATENT DOCUMENTS

| | | | | |
|---|---|---|---|---|
| CA | 1068052 A1 | 12/1979 | | |
| CA | 2485716 A1 | * 4/2005 | ............. | A61L 27/10 |

(Continued)

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.

(Continued)

*Primary Examiner* — Christian A Sevilla
(74) *Attorney, Agent, or Firm* — Pilloff Passino & Cosenza LLP; Martin J. Cosenza

(57) ABSTRACT

The present invention relates to a percutaneous implant abutment for bone anchored implant devices adapted to be anchored in the craniofacial region of a person, such as bone anchored hearing aids. The abutment comprises a skin penetration body having a skin contacting surface. The skin contacting surface has been modified.

21 Claims, 2 Drawing Sheets

(56) References Cited

U.S. PATENT DOCUMENTS

| | | |
|---|---|---|
| 4,038,990 A | 8/1977 | Thompson |
| 4,052,754 A | 10/1977 | Homsy |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| D267,541 S | 1/1983 | Kanemitsu |
| 4,414,701 A | 11/1983 | Johnson |
| 4,498,461 A | 2/1985 | Hakansson |
| 4,596,971 A | 6/1986 | Hirabayashi et al. |
| 4,606,329 A | 8/1986 | Hough |
| 4,610,621 A | 9/1986 | Taber et al. |
| 4,612,915 A | 9/1986 | Hough et al. |
| 4,628,907 A | 12/1986 | Epley |
| 4,645,504 A | 2/1987 | Byers |
| 4,676,772 A | 6/1987 | Hooven |
| 4,696,287 A | 9/1987 | Hortmann et al. |
| 4,726,378 A | 2/1988 | Kaplan |
| 4,731,718 A | 3/1988 | Sheu |
| 4,736,747 A | 4/1988 | Drake |
| 4,818,559 A | 4/1989 | Hama et al. |
| RE32,947 E | 6/1989 | Dormer et al. |
| 4,868,530 A | 9/1989 | Ahs |
| 4,915,628 A | 4/1990 | Linkow et al. |
| 4,917,504 A | 4/1990 | Scott et al. |
| 4,918,745 A | 4/1990 | Hutchison |
| 4,920,679 A | 5/1990 | Sarles et al. |
| 5,014,592 A | 5/1991 | Zweig et al. |
| 5,015,224 A | 5/1991 | Maniglia |
| 5,026,397 A | 6/1991 | Aoki et al. |
| 5,049,074 A | 9/1991 | Otani et al. |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,314,453 A | 5/1994 | Jeutter |
| D348,067 S | 6/1994 | Lucey et al. |
| 5,456,654 A | 10/1995 | Ball |
| 5,456,717 A | 10/1995 | Zweymuller et al. |
| 5,549,658 A | 8/1996 | Shannon et al. |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,645,580 A | 7/1997 | Moaddeb et al. |
| 5,716,407 A | 2/1998 | Knapp et al. |
| 5,735,790 A | 4/1998 | Håkansson et al. |
| 5,749,912 A | 5/1998 | Zhang et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,906,635 A | 5/1999 | Maniglia |
| 5,913,815 A | 6/1999 | Ball et al. |
| 5,951,601 A | 9/1999 | Lesinski et al. |
| 5,971,334 A | 10/1999 | Crawshaw et al. |
| 6,011,993 A | 1/2000 | Tziviskos et al. |
| 6,040,762 A | 3/2000 | Tompkins |
| 6,073,973 A | 6/2000 | Boscaljon et al. |
| 6,138,681 A | 10/2000 | Chen et al. |
| 6,157,278 A | 12/2000 | Katznelson et al. |
| 6,157,281 A | 12/2000 | Katznelson et al. |
| 6,171,229 B1 | 1/2001 | Kroll et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,275,736 B1 | 8/2001 | Kuzma et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Faltys et al. |
| 6,313,551 B1 | 11/2001 | Hazelton |
| 6,348,070 B1 | 2/2002 | Teissl et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 | 1/2003 | Woods |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,589,216 B1 | 7/2003 | Abbott et al. |
| 6,668,065 B2 | 12/2003 | Lee et al. |
| 6,705,985 B2 | 3/2004 | Easter et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,091,806 B2 | 8/2006 | Zimmerling et al. |
| 7,190,247 B2 | 3/2007 | Zimmerling |
| 7,200,504 B1 | 4/2007 | Fister |
| 7,225,028 B2 | 5/2007 | Della Santina et al. |
| 7,231,252 B2 | 6/2007 | Duncan et al. |
| 7,338,028 B2 | 3/2008 | Zimmerling et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |
| 7,806,693 B2 | 10/2010 | Hurson |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,469,908 B2 | 6/2013 | Asfora |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 | 1/2014 | Zimmerling et al. |
| 8,734,475 B2 | 5/2014 | Ekvall et al. |
| 8,744,106 B2 | 6/2014 | Ball |
| 8,758,394 B2 | 6/2014 | Zimmerling et al. |
| 8,768,480 B2 | 7/2014 | Charvin |
| 8,897,475 B2 | 11/2014 | Ball et al. |
| 8,983,102 B2 | 3/2015 | Crawford et al. |
| 9,005,202 B2 * | 4/2015 | Andersson ............ A61F 2/0077 606/76 |
| 9,022,917 B2 | 5/2015 | Kasic et al. |
| RE45,701 E | 9/2015 | Zimmerling et al. |
| 9,144,676 B2 | 9/2015 | Gibson et al. |
| 9,888,329 B2 * | 2/2018 | Andersson ............ A61F 2/0077 |
| 2001/0021805 A1 | 9/2001 | Blume et al. |
| 2001/0047175 A1 | 11/2001 | Doubler et al. |
| 2002/0076071 A1 | 6/2002 | Single |
| 2002/0099421 A1 | 7/2002 | Goldsmith et al. |
| 2003/0120202 A1 | 6/2003 | Gordon |
| 2003/0139782 A1 | 7/2003 | Duncan |
| 2003/0171787 A1 | 9/2003 | Money et al. |
| 2003/0176866 A1 | 9/2003 | Westerkull |
| 2003/0181956 A1 | 9/2003 | Duncan et al. |
| 2004/0012470 A1 | 1/2004 | Zimmerling et al. |
| 2004/0059423 A1 | 3/2004 | Barnes et al. |
| 2004/0132143 A1 | 7/2004 | DeAngelis et al. |
| 2004/0167450 A1 | 8/2004 | Buckman et al. |
| 2004/0204686 A1 | 10/2004 | Porter et al. |

(56) References Cited

U.S. PATENT DOCUMENTS

| | | |
|---|---|---|
| 2004/0215164 A1 | 10/2004 | Abbott et al. |
| 2004/0260361 A1 | 12/2004 | Gibson |
| 2005/0001703 A1 | 1/2005 | Zimmerling |
| 2005/0004629 A1 | 1/2005 | Gibson et al. |
| 2005/0026113 A1 | 2/2005 | Chen et al. |
| 2005/0062567 A1 | 3/2005 | Zimmerling et al. |
| 2005/0106534 A1 | 5/2005 | Gahlert |
| 2005/0113834 A1 | 5/2005 | Breitenstien et al. |
| 2005/0142163 A1 | 6/2005 | Hunter et al. |
| 2005/0159791 A1 | 7/2005 | Daly et al. |
| 2005/0171579 A1 | 8/2005 | Tasche et al. |
| 2006/0030905 A1 | 2/2006 | Malaver |
| 2006/0050913 A1 | 3/2006 | Westerkull |
| 2006/0093175 A1 | 5/2006 | Westerkull |
| 2006/0184212 A1 | 8/2006 | Faltys et al. |
| 2006/0241592 A1 | 10/2006 | Myerson et al. |
| 2006/0244560 A1 | 11/2006 | Zimmerling et al. |
| 2007/0009853 A1 | 1/2007 | Pitulia |
| 2007/0126540 A1 | 6/2007 | Zimmerling |
| 2007/0208403 A1 | 9/2007 | Della Santina et al. |
| 2007/0270631 A1 | 11/2007 | Nelson et al. |
| 2008/0221641 A1 | 9/2008 | Hochmair |
| 2009/0069869 A1 | 3/2009 | Stouffer et al. |
| 2009/0082817 A1 | 3/2009 | Jinton et al. |
| 2009/0287278 A1 | 11/2009 | Charvin |
| 2010/0249784 A1 | 9/2010 | Andersson |
| 2011/0004278 A1 | 1/2011 | Aghassian |
| 2011/0022120 A1 | 1/2011 | Ball et al. |
| 2011/0264172 A1 | 10/2011 | Zimmerling et al. |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0172659 A1 | 7/2012 | Ball et al. |
| 2012/0238799 A1 | 9/2012 | Ball et al. |
| 2012/0296155 A1 | 11/2012 | Ball |
| 2012/0323066 A1 | 12/2012 | Cho et al. |
| 2012/0330378 A1 | 12/2012 | Crawford et al. |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0110198 A1 | 5/2013 | Stoffaneller |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121447 A1 | 5/2014 | Kasic et al. |
| 2014/0213139 A1 | 7/2014 | Ferguson |
| 2014/0275736 A1 | 9/2014 | Ruppersberg et al. |
| 2014/0302741 A1 | 10/2014 | Whittaker |
| 2014/0343626 A1 | 11/2014 | Thenuwara et al. |
| 2015/0087892 A1 | 3/2015 | Tourrel et al. |
| 2015/0157778 A1 | 6/2015 | Ishiyama et al. |
| 2016/0008596 A1 | 1/2016 | Gibson et al. |
| 2016/0144170 A1 | 5/2016 | Gibson et al. |
| 2016/0361537 A1 | 12/2016 | Leigh et al. |
| 2017/0312503 A1 | 11/2017 | Leigh et al. |

FOREIGN PATENT DOCUMENTS

| | | |
|---|---|---|
| EP | 0367354 A1 | 5/1990 |
| GB | 414579 A | 8/1934 |
| GB | 2266045 A | 10/1993 |
| JP | H06192852 A | 7/1994 |
| WO | 9855049 A1 | 12/1998 |
| WO | 0197718 A1 | 12/2001 |
| WO | 0209622 A1 | 2/2002 |
| WO | 02056637 A1 | 7/2002 |
| WO | 2004091432 A2 | 10/2004 |
| WO | 2005037153 A1 | 4/2005 |

OTHER PUBLICATIONS

Med-El, "Magnetic Resonance Imaging (MRI)," believed to be available in Jan. 2016.

D. Cuda et al., "Focused tight dressing does not prevent cochlear implant magnet migration under 1.5 Tesla MRI," believed to be available in Jan. 2016.

International Search Report for PCT/SE2008/000337 dated Jul. 16, 2008.

* cited by examiner

IMPLANT ABUTMENT

CROSS-REFERENCE TO RELATED APPLICATIONS

This application is a continuation application of U.S. application Ser. No. 14/685,048, filed Apr. 13, 2015, which is a continuation application of U.S. application Ser. No. 12/601,801, filed on May 21, 2010, now U.S. Pat. No. 9,005,202, which is a national stage application under 35 USC § 371 (c) of PCT Application No. PCT/SE2008/000337, entitled "IMPLANT ABUTMENT," filed on May 20, 2008, which claims priority from Swedish Patent Application No. 0701244-6, filed on May 24, 2007. This application is related to commonly owned and co-pending U.S. Utility Patent Application entitled "VIBRATOR FOR BONE CONDUCTING HEARING DEVICES," filed Nov. 24, 2009, which is a national stage application of PCT Application No. PCT/SE2008/000336, filed May 21, 2008. This application is also related to commonly owned and co-pending U.S. Utility Patent Application entitled "ANCHORING ELEMENT" which is a national stage application under 35 USC § 371 (c) of PCT Application No. PCT/SE2008/000338, filed on May 21, 2008. The entire disclosure and contents of the above applications are hereby incorporated by reference herein in their entirety.

BACKGROUND

Field of the Invention

The present invention relates generally to bone anchored implant devices, and more particularly, to a percutaneous implant abutment for bone anchored implant devices adapted to be anchored in the craniofacial region of a person.

Related Art

There are a variety of medical devices that include a bone anchored implant device. An example of such medical devices is the, bone conduction hearing aid devices such as bone anchored hearing implants. An example of a bone anchored hearing implant is the Baha®, commercially available from Cochlear Bone Anchored Solutions AB in Goteborg, Sweden. The Baha® and other bone anchored implant devices comprise an external unit which transforms sound to mechanical vibrations which are conducted via the abutment and the fixture into the bone of the skull. The vibrations are transmitted mechanically via the skull bone directly to the inner ear of a person with impaired hearing and allows for the hearing organ to register the sound. A hearing aid device of the BAHA® type is connected to an anchoring element in the form of an implanted titanium screw installed in the bone behind the external ear. Sound is transmitted via the skull bone to the cochlea irrespective of a disease in the middle ear. The bone anchoring principle means that the skin is penetrated which makes the vibratory transmission very efficient.

This type of hearing aid device has been a revolution for the rehabilitation of patients with certain types of impaired hearing, but also as anti-stuttering means. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and in SE 9702164-6 it is described a one-piece implant of this type, in which the fixture is integrated with a first coupling device. In WO 2005/037153 it is described how this type of hearing aid device can be used as an anti-stuttering device.

A well known problem with percutaneous implants is the infections and inflammation at the skin-implant interface. The infections are a result of bacterial colonization occurring at the area around the interface. There is generally a lack of integration of the skin to the implant which results in a gap between the two. This gap is unfortunately an ideal environment for the bacteria and if this zone is not properly managed, it is likely that an infection will occur. By creating an integration of the skin to the implant the adverse skin reactions associated with bone anchored percutaneous implants are expected to be reduced.

Creating integration between the skin and the implant requires that the implant is suitable for this purpose and that the soft tissue does not dissociate itself from the skin penetrating implant abutment by encapsulating the abutment in fibrous tissue.

In the field of dental implants it is previously known to use different types of abutments which penetrate the oral mucosa. However, it should be understood that there is a physiological difference between breaching the skin barrier compared to the oral mucosa. In the oral cavity the skin is not involved and there is another type of force situation. In contrast to dental implants the present invention relates to extraoral implants.

It is recognized that bone anchored percutaneously implants are subjected to mostly shear forces, while percutaneously implants which are not bone anchored are subjected to several other types of forces, such as pull and torsion. Such different types of forces are also mostly involved in dental applications. Mostly shear forces are especially the case for implants with inherent movements such as bone anchored hearing implants due to the generation of vibratory movements.

It is also recognized that the effect that the shear forces has on the skin leads to tissue damage not only from a mechanical point of view but, more importantly, an indirect biological reaction which leads to foreign body reaction or dissociation from the material (encapsulation of the implant by fibrous tissue, etc). Some reactions are acute and some are noticed after several weeks.

SUMMARY

In one aspect of the present invention, a percutaneous implant for bone anchored implant devices adapted to be anchored in the craniofacial region of a person is provided. The implant comprises: a screw-shaped bone anchoring element; an abutment, comprising: a skin penetration body having a skin contacting surface; and a biocompatible coating disposed on the skin contacting surface.

BRIEF DESCRIPTION OF THE DRAWINGS

Illustrative embodiments of the present invention will be described herein with reference to the accompanying figures, in which.

DETAILED DESCRIPTION

The present invention relates generally to bone anchored implant devices, and more particularly, to a percutaneous implant abutment for bone anchored implant devices adapted to be anchored in the craniofacial region of a person, such as bone anchored hearing aids. Implant devices of this type normally comprise a screw-shaped bone anchoring element (fixture) for permanent anchorage in the bone tissue and an abutment sleeve for skin penetration. The complete structure can either be in one piece or the skin penetrating abutment could be connected to the fixture prior, during or after the implantation procedure by means of a screw connection or the like.

Figure 1:
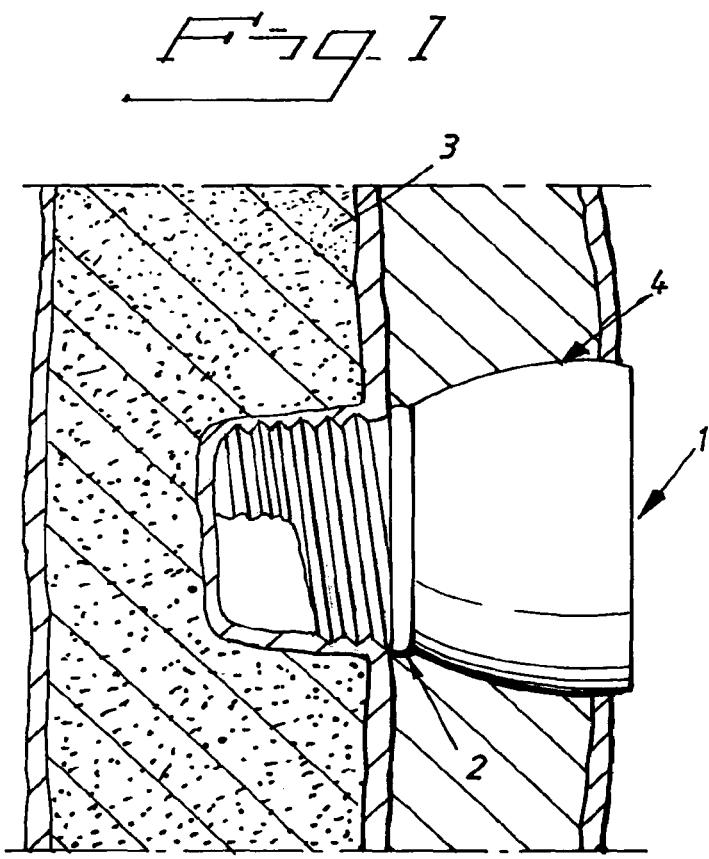
FIG. 1 illustrates an implant according to one embodiment of the present invention anchored in the bone in the craniofacial region of a person.

FIG. 1 illustrates a percutaneous implant 1 in accordance with embodiments of the present invention anchored in the bone in the craniofacial region of a person. The implant is may be used for a bone anchored hearing aid or the like. The implant comprises a screw-shaped bone anchoring element (fixture) 2 for permanent anchorage in the bone tissue 3 and an abutment device 4 for skin 5 penetration. The complete structure can either be in one piece or the skin penetrating abutment 4 could be connected to the fixture prior, during or after the implantation procedure by means of a screw connection or the like. The screw-shaped anchoring element, the so-called fixture 2 is made of titanium which has a known ability to integrate with the surrounding bone tissue, so-called osseointegration. The fixture has a threaded part 2a which is intended to be installed into the skull bone and a flange 2b which functions as a stop when the fixture is installed into the skull bone. The apical part of the fixture has a known tapping ability with in this case three self-tapping edges 2c. A fixture of this type is described in the above-mentioned SE 0002627-8 and will therefore not be described in any detail here.

The skin penetrating part, the abutment 4 of the implant, comprises a substantially conical abutment sleeve. Conical abutment sleeves are previously known per se as separate components or as an integral part with the fixture, a one-piece implant. The abutment sleeve is provided with a first coupling part in order to cooperate with a second coupling part (not shown) by means of snap-in action or the like.

According to embodiments of the present invention the shear modulus of the skin contacting part of the percutaneous implant abutment 4 has been reduced. Preferably the shear modulus should be less than approximately 35 GPa.

Figure 2:
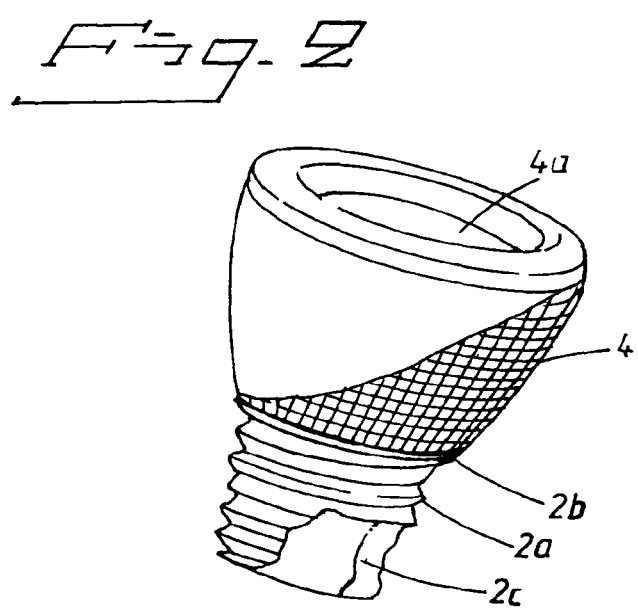
FIG. 2 illustrates an implant according to embodiments of the present invention for bone anchorage.

Specifically, the shear modulus is reduced by a modification of the surface of the skin contacting part of the percutaneous implant abutment, illustrated by the structured abutment surface in FIG. 2. According to a preferred embodiment the surface of the skin contacting part of the percutaneous implant abutment is coated with a biocompatible polymer or a ceramic material with a thickness of approximately 0.001 µm to approximately-50 µm. The coating is applied in such a way that non-interconnected pores or crevices are created. Generally the coating should be applied in such a way that a structured surface such as a porous surface or a surface with indentations or a fibrous surface is obtained. A typical porous surface is illustrated by the SEM picture in FIG. 4.

The polymer coating is comparatively soft and decreases the shear stresses on the skin. In certain embodiments, a layer of a porous polymer is used for the coating with a thickness of about 30 nm. Such design is allowing the skin to heal into the polymer matrix.

Also a polymer containing a pharmaceutical drug that increases the production of extra-cellular matrix proteins in the soft tissue, such as collagen or keratin, might be used. The increased stability of the tissue increases the resistance to shear stress.

Also other types of materials might be used for increasing the skin tissue integration. Specifically, chemical substances such as pharmaceutical drugs and antioxidants, or biochemical substances such as proteins, biopolymers, growth factors, DNA, RNA or biominerals might be used. These substances are then associated to the implant with a purpose of increasing the amount of, or number of connections to extra cellular matrix proteins. Antibiotic, steroid or anti-inflammatory substances might also be used.

As an alternative to said coatings or substances, or in combination, a surface enlargement treatment can be provided to the surface of the skin contacting part of the percutaneous implant in order to increase the surface roughness. Such treatment can be achieved by using techniques that includes grit-blasting, polishing, micro-machining, laser treatment, turning, anodic oxidation, oxidation, chemical etching, sintering or plasma deposition of a titanium surface. Preferably such treatment should result in a 10% surface increase, compared to a conventional machined surface and a roughness value Sa of approximately 0.5 µm to approximately-10 µm, measured by means of White Light Interferometry.

Figure 3:
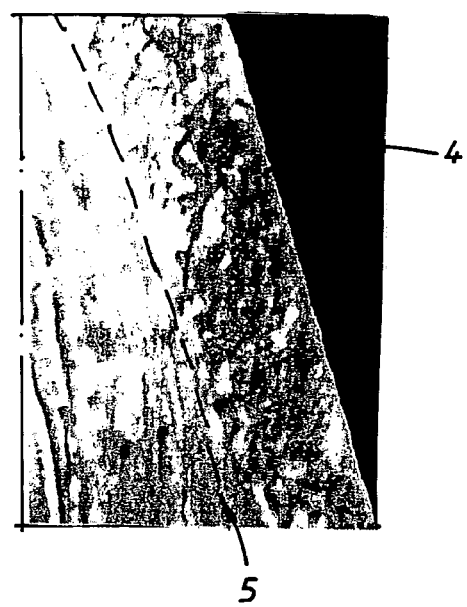
FIG. 3 is a LM picture of the interface between the skin and the contacting part of the implant abutment.

FIG. 3 is a LM picture of the interface between the skin 5 and the contacting part of the implant abutment 4 of a polyurethane coated titanium material. The figure illustrates the situation after a healing period of 8 days and indicates a substantial integration of the abutment into the skin 5.

Figure 4:
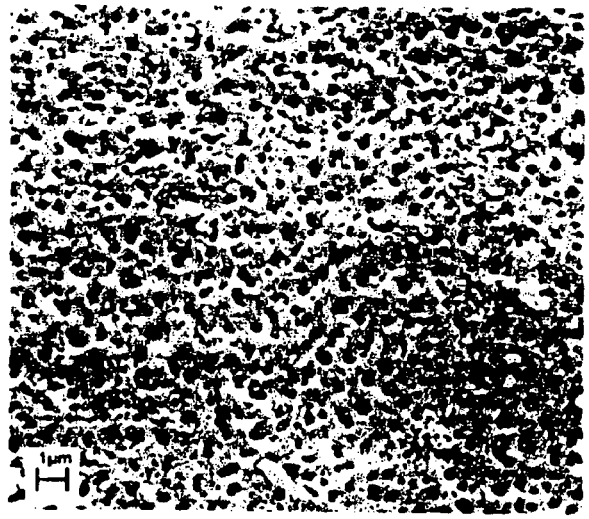
FIG. 4 is a SEM picture of the surface structure of the skin contacting part of the implant abutment.

FIG. 4 is a SEM picture of the surface structure of the skin contacting part of the implant abutment having an anodically oxidized surface.

It should be understood that only that part of the abutment surface which is in contact with the skin need to be modified. Other parts of the abutment such as the lower and upper end surfaces, i.e. the surfaces connected to the fixture and the coupling device respectively, might have a conventional, machined and/or polished surface.

According to one embodiment of the present invention, the surface of the skin contacting part of the percutaneously implant abutment is coated with a biocompatible polymer with a thickness of approximately 0.001 µm-to approximately 50 µm. According to a another embodiment, the surface of the skin contacting part of the percutaneously implant abutment is coated with a ceramic material with a thickness of 0.001 µm-to approximately 50 µm.

According to another embodiment, a surface enlargement treatment has been provided to the surface of the skin contacting part of the percutaneously implant abutment. Preferably a 10% surface increase, compared to a conventional machined surface, is created resulting in a roughness value Sa of 0.5 µm-to approximately 10 µm.

It should be understood that there are percutaneous implant as such that are made of polymers (catheters etc) but they are not bone anchored and they are not exposed to the typical shear forces that are the case for implants with inherent movements such as bone anchored hearing implants due to the generation of vibratory movements.

An advantage of embodiments of the present invention is to provide an implant abutment in which the shear forces between the implant abutment and the skin have been reduced. This improves wound healing and integration around bone anchored percutaneous implants.

According to another feature of embodiments of the present invention, the shear modulus of the skin contacting part of the percutaneously implant abutment is reduced. Preferably the shear modulus should be less than approximately 35 GPa.

In certain embodiments, the implant design includes a flange or a skirt perpendicular to the abutment orientation in order to mechanically increase the surface area and stability and thereby also reduce the shear stress on the implant-skin interface. Also the implant design might include one or more retention grooves or waists. Otherwise, however, the abutment should be designed without any sharp edges or corners in order to simplify the surface modification procedure.

Further features and advantages of the present invention are described in commonly owned and co-pending U.S. Utility Patent Application entitled "VIBRATOR FOR BONE CONDUCTING HEARING DEVICES," filed Nov. 24, 2009, which is a national stage application of PCT Application No. PCT/SE2008/000336, filed May 21, 2008; and commonly owned and co-pending U.S. Utility Patent Application entitled "ANCHORING ELEMENT" which is a national stage application under 35 USC § 371 (c) of PCT Application No. PCT/SE2008/000338, filed on May 21, 2008. The content of these applications are hereby incorporated by reference herein.

It will be appreciated by persons skilled in the art that numerous variations and/or modifications may be made to the invention as shown in the specific embodiments without departing from the spirit or scope of the invention as broadly described. Specifically it should be understood that any combinations of the said surface modifications could be used, e.g. using composites, structured ceramic coatings, polymer/pharmaceutical drug coatings, anodized flange etc. The present embodiments are, therefore, to be considered in all respects as illustrative and not restrictive.

What is claimed is:

1. A percutaneous implant for a bone anchored implant device adapted to be anchored to a bone of a recipient, comprising:
    an abutment, including:
        a skin penetration body having a skin contacting surface; and
        a biocompatible coating disposed on the skin contacting surface,
        wherein the abutment is configured for interaction with an external unit which transforms sound to mechanical vibrations which are conducted to the abutment to evoke a hearing percept.

2. The percutaneous implant of claim 1, wherein the biocompatible coating comprises a biocompatible polymer having a thickness of equal to or greater than approximately 0.001 micrometers.

3. The implant according to claim 1, wherein the coating is configured to increase production of extra-cellular matrix proteins in soft tissue of the skin.

4. A percutaneous abutment for a bone anchored implant device adapted to be anchored to a bone of a recipient, comprising:
    a skin penetration body having a skin contacting surface, wherein the abutment is configured such that the skin contacting surface is configured to integrate with recipient skin overlying the bone of the recipient, wherein
    at least one of:
        a threaded portion configured to be screwed into bone is mechanically attached to the abutment, wherein the threaded portion is a separate component from the abutment; or
        the abutment is configured for interaction with an external unit which transforms sound to mechanical vibrations which are conducted to the abutment to evoke a hearing percept.

5. The percutaneous abutment of claim 4 wherein:
    the abutment is configured to increase production of extra-cellular matrix proteins in soft tissue of the recipient skin, thereby integrating the abutment with the recipient skin overlying the bone of the recipient.

6. The percutaneous abutment of claim 4 wherein:
    the abutment is coated with a ceramic.

7. A percutaneous implant for a bone anchored implant device adapted to be anchored to a bone of a recipient, comprising:
    an abutment, including:
        a skin penetration body having a skin contacting surface; and
        a threaded portion configured to screw into bone, wherein
    the implant includes a surface of a modified configuration, and
        the abutment is configured for interaction with an external unit which transforms sound to mechanical vibrations which are conducted to the abutment to evoke a hearing percept.

8. The implant of claim 7, wherein:
    the modified configuration is a coating.

9. The implant of claim 7, wherein:
    the implant is implanted in a recipient such that it is fixed to bone of the recipient, and wherein at least a portion of the implant is integrated with tissue of the recipient.

10. The implant of claim 7, wherein:
    the implant is implanted in a recipient such that it is fixed to bone of the recipient; and
    the modified surface has reduced shear forces between the abutment and skin of the recipient relative to that which would be the case in the absence of the modified surface.

11. The implant device of claim 7, wherein:
    the modified configuration is that resulting from a surface enlargement treatment.

12. The implant device of claim 7, wherein:
    the implant is implanted in a recipient such that it is fixed to bone of the recipient; and
    skin of the recipient overlying the bone of the recipient is healed into the surface of a modified configuration.

13. The percutaneous implant of claim 1, wherein the biocompatible coating stops at a location at about where the implant would enter bone when anchored to bone.

14. The implant of claim 7, wherein:
    the surface of the modified configuration includes at least one of porous surface features, indentations or fibrous surface features configured to integrate with recipient skin overlying the bone of the recipient.

15. The percutaneous implant of claim 1, wherein the implant incudes a threaded portion configured to screw into bone, and wherein most of the biocompatible coating, based on surface area, is located away from the threaded portion.

16. The percutaneous implant of claim 1, further comprising a threaded portion configured to be screwed into bone, wherein the threaded portion is a separate component from the abutment that is mechanically connected to the abutment.

17. The percutaneous implant of claim 1, wherein the implant is implanted in a recipient and has been so implanted for eight (8) days, and wherein the abutment is substantially integrated into skin at the biocompatible coating.

18. The implant of claim 7, wherein:
   the surface of the modified configuration is established by a surface enlargement treatment.

19. The implant of claim 7, wherein:
   the surface of the modified configuration is established by laser treatment.

20. The implant according to claim 1, wherein the biocompatible coating is configured to integrate with skin contacting the skin contacting surface.

21. The implant according to claim 7, wherein the modified surface is configured to integrate with skin contacting the skin contacting surface.

* * * * *